United States Patent
Kompaniets et al.

(10) Patent No.: US 10,436,709 B2
(45) Date of Patent: Oct. 8, 2019

(54) CALIBRATION UNIT FOR OPTICAL DETECTOR

(71) Applicant: Endress+Hauser Conducta Inc., Anaheim, CA (US)

(72) Inventors: Iouri Kompaniets, Running Springs, CA (US); Budi Komala, Anaheim, CA (US); Paul Mark Gonda Cacha, Anaheim, CA (US)

(73) Assignee: Endress+Hauser Conducta Inc., Anaheim, CA (US)

( * ) Notice: Subject to any disclaimer, the term of this patent is extended or adjusted under 35 U.S.C. 154(b) by 9 days.

(21) Appl. No.: 15/875,147

(22) Filed: Jan. 19, 2018

(65) Prior Publication Data
US 2019/0226986 A1 Jul. 25, 2019

(51) Int. Cl.
*G01N 21/27* (2006.01)
*G01N 21/31* (2006.01)
*G01J 3/02* (2006.01)

(52) U.S. Cl.
CPC .......... *G01N 21/278* (2013.01); *G01J 3/0202* (2013.01); *G01N 21/31* (2013.01)

(58) Field of Classification Search
CPC .............................. H01S 3/1024; G01J 3/0202
See application file for complete search history.

(56) References Cited

U.S. PATENT DOCUMENTS

| 4,583,859 | A | * | 4/1986 | Hall, II | B01D 46/46 250/236 |
| 5,760,911 | A | * | 6/1998 | Santschi | G01N 21/534 356/438 |
| 5,905,271 | A | * | 5/1999 | Wynn | G01J 3/02 250/573 |
| 6,512,223 | B1 | * | 1/2003 | Wynn | G01J 1/08 250/226 |
| 6,977,365 | B1 | * | 12/2005 | Wynn | G01J 1/02 250/216 |
| 9,279,746 | B2 | * | 3/2016 | Wynn | G01N 21/05 |
| 9,404,849 | B2 | * | 8/2016 | Wynn | G01N 21/05 |
| 10,066,992 | B2 | * | 9/2018 | Ando | G01J 3/28 |

\* cited by examiner

*Primary Examiner* — Shawn Decenzo
(74) *Attorney, Agent, or Firm* — Christopher R. Powers; PatServe (57) ABSTRACT

A device for calibrating an in-line sensor is disclosed, including a housing having a first aperture and a second aperture arranged along an optical path extending through the housing, a first filter and a second filter disposed within the housing such that the filters are moveable from an operating position to a calibration position. In the calibration position the filters are arranged in the optical path and the housing includes a connection adjacent each of the first aperture and the second aperture, the connection structured to enable the housing to be reversibly attached to a flow cell, a detector and a light source of an in-line sensor.

20 Claims, 5 Drawing Sheets

CALIBRATION UNIT FOR OPTICAL DETECTOR

TECHNICAL FIELD

The present disclosure generally relates to photometric analyzers, in particular calibration filters for use in a photometric analyzer such as an in-line optical sensor.

BACKGROUND

In production processes, optical measurements can be performed in gases, liquids, solids, and multiphase mixtures to determine certain properties of the production process or about a substance formed as a product of the process. From such measurements, values of measurands correlating to the concentration of educts and/or additives of the process can be determined. For example, in a chemical production process, concentrations of reactants used in the production process and/or the concentration of products produced in the process within a process medium can be monitored, and the process sequence can be controlled and/or regulated based upon the measured data obtained.

The process medium is generally contained in a process container, such as a reactor, a fermenter, a duct or a pipe line. Sensors capable of performing such measurements may be attached to the process container. Alternatively, the process medium may be routed through a flow cell of the sensor to analyze at least a sample from the process container. Such sensors may be referred to as in-line sensors. Conventional in-line sensors are commonly used to evaluate various fluid properties such as concentration through optical measurements of the medium in the process. Such optical measurements may be performed by optical sensors that operate upon absorption of light from a light source in part of optical spectra by the medium as measured by a detector.

Optical sensors, including in-line optical sensors, require periodic calibration to assure required accuracy and dynamic range. One common calibration method uses neutral density (ND) optical filters of known absorption positioned at any point in the optical path between the light source and detector of the sensor. Such ND filters allow only a known portion of the light form the light source, which is associated with a particular absorption (or transmission) value by the detector. After the calibration procedure, the ND filter is moved out of optical path. In certain applications, such ND filters may be traceable calibration filters per the requirements and specifications of the National Institute of Standards and Technology (NIST). Such filters are subject to deterioration with use and exposure to the environment and thus must be re-certified periodically.

U.S. Pat. No. 5,905,271 discloses an in-line optical sensor that can be utilized in a wide variety of applications (e.g. Spectro radiometers, radiometers, colorimeters, turbidimeters, refractometers, and ultrasonic flow and particle sensing devices) for monitoring photometric the properties of a fluid product stream. Such instruments generally have a light source and a detector positioned on opposite sides of the product stream, with the light source directing a beam of light through the product stream to the detector. The light can be in the ultraviolet, visible or infrared spectrums, and the term light is used herein as including all three.

U.S. Pat. No. 6,512,223 discloses a photometric detector assembly which includes a pair of NIST traceable calibration filters enclosed within a sealed housing and means outside the housing for manually moving the filters into and out of the path of a beam between calibration and normal operating positions. This system can be calibrated to a high degree of accuracy, and being in sealed housing and exposed to the beam only on a limited basis, the filters do not need to be cleaned and/or replaced as often as they otherwise would. However, it movement the filters between the calibration and operating positions is a manual operation.

Often, it is not convenient to use a photometric detector such as the one disclosed in U.S. Pat. No. 6,512,223 due to size constraints within the facilities of the process to be monitored or due to cost constraints. In other circumstances, the process may include in-line optical sensors that do not have built-in calibration filters, thus requiring the in-line optical sensors to be removed from the process for calibration and then reinstalled. Accordingly, there remains a need for further contributions in this area of technology.

BRIEF SUMMARY

According to at least one aspect of the present disclosure, a device for calibrating an in-line sensor includes a housing having a first aperture and a second aperture therethrough, the first aperture and the second aperture arranged along an optical path extending through the housing, a first filter disposed within the housing such that the first filter is moveable from an operating position to a calibration position, wherein in the calibration position the first filter is arranged in the optical path, and a second filter disposed within the housing such that the second filter is moveable, independently from and adjacent to the first filter, from an operating position to a calibration position, wherein in the calibration position the second filter is arranged in the optical path. The housing includes a connection adjacent each of the first aperture and the second aperture, the connections structured to enable the housing to be reversibly attached to a flow cell, a detector and a light source of an in-line sensor.

In an embodiment, the first filter is attached to a rotatable first shaft such that the first filter is rotatable from the operating position to the calibration position via rotation of the first shaft. In certain such embodiments, the first filter is connected to a first arm that is connected to the first shaft such that rotation of the first shaft enables rotation of the first filter, and the first shaft extends through the first wall of the housing. In a further embodiment, the second filter is attached to a rotatable second shaft such that the second filter is rotatable from the operating position to the calibration position via rotation of the second shaft. In certain such embodiments, the second filter is connected to a second arm that is connected to the second shaft such that rotation of the second shaft enables rotation of the second filter, and wherein the second shaft extends through the first wall of the housing.

In any least one embodiment, the first filter and the second filter are neutral-density filters. The first filter and the second filter are calibration elements traceable to standards maintained by the National Institute of Standards and Technology.

In any least one embodiment, each connection is a threaded connection complementary to threaded connections of the flow cell, the detector and the light source. In an embodiment, the housing includes a fitting, which defines the first aperture, extending from a first wall of the housing, and wherein the fitting includes the connection adjacent the first aperture. A second wall of the housing includes the second aperture, and wherein the second wall includes the connection adjacent the second aperture on an edge of the second wall. In certain embodiments, the device further includes a first actuator connected to the first arm and a second actuator connected to the second arm, the first actuator and second actuator each remotely operable.

According to another aspect of the present disclosure, an in-line sensor for determining a parameter of a process medium flow includes a light source embodied to generate light along an optical path, the light source including a source aperture disposed along the optical path and a connection adjacent the source aperture, a detector arranged in the optical path and embodied to detect the light generated by the light source, the detector including a detector aperture disposed along the optical path and a connection adjacent the detector aperture, a flow cell disposed between and reversibly attachable via complementary connections to the light source and the detector, the flow cell having opposing sides including opposing apertures therethrough and in the optical path adjacent the complementary connections, the flow cell further embodied to enable a fluid to be analyzed to flow along a flow path, the flow path generally orthogonal to the optical path, and the calibration unit reversibly attachable to either side of the flow cell via the complementary connections and disposed between the light source and the detector and in the optical path. In an embodiment, the in-line sensor further includes a spacer in substitution of the calibration unit, the spacer including a spacer housing having a first spacer aperture and a second spacer aperture therethrough, the first spacer aperture and the second spacer aperture arranged along an optical path extending through the housing, wherein the spacer housing includes a connection adjacent each of the first spacer aperture and the second spacer aperture, the connection structured to enable the spacer to be reversibly attached to the flow cell, the detector and the light source, and wherein the spacer has the same optical path length as the calibration unit. In certain embodiments, each connection is a threaded connection complementary to threaded connections of the flow cell, the detector and the light source.

BRIEF DESCRIPTION OF THE DRAWINGS

The described embodiments and other features, advantages and disclosures contained herein, and the manner of attaining them, will become apparent and the present disclosure will be better understood by reference to the following description of various embodiments of the present disclosure taken in junction with the accompanying drawings, wherein.

DETAILED DESCRIPTION

The present application discloses various embodiments of a calibration unit and methods for using and constructing the same. The calibration unit enables the calibration of in-line sensor without needing to remove the sensor from the process in which it has been employed. Relative to conventional in-line sensors, the disclosed calibration unit may be employed in a wider variety of processes and enables more convenient calibration and better flexibility for reliably monitoring the process without the cost of replacing older sensors. According to one aspect of the present disclosure, an in-line sensor including the calibration unit is disclosed. For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1:
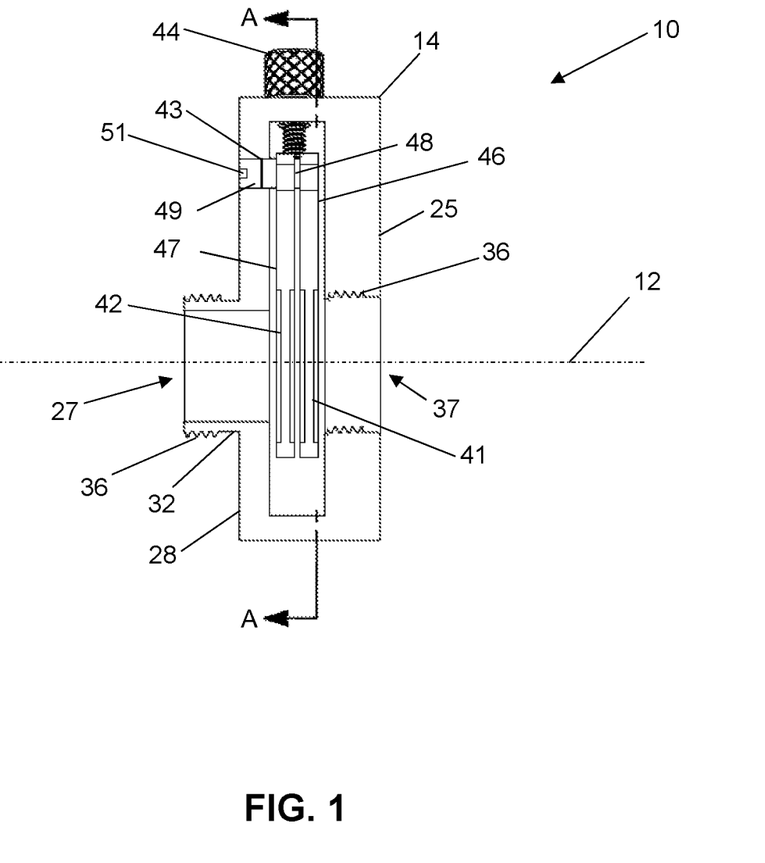
FIG. 1 shows a cross-sectional view of an embodiment of a calibration unit according to the present disclosure.

FIG. 1 shows a calibration unit 10 according to at least one embodiment of the present disclosure. The calibration unit 10 includes a housing 14 embodied to contain a first filter 41 and a second filter 42. The housing 14 includes a first wall 28 having a first aperture 27 formed therethrough and a second wall 25 having a second aperture 37 formed therethrough. The first aperture 27 and the second aperture 37 are aligned along an optical path 12 that extends through the housing 14. Adjacent the first aperture 27, the housing 14 may include a fitting 32 extending from the first wall 28, as shown in FIG. 1. The unit fitting 32 may include a first unit connection 36 adjacent the aperture 27. The housing 14 may further include a second unit connection 36 on an edge of the second wall 25 defining the aperture 37.

The unit connections 36 are configured to enable various components to reversibly attach to the calibration unit 10. In at least one embodiment, the unit connections 36 are threaded connections. In alternative embodiments, the unit connections 36 may be another suitable, reversible attachment means. Other suitable, reversible attachment means, for the calibration unit 10 and for other components described herein, include at least clamps, clips, rings, snaps, pins, ties, grommets and fasteners.

The first filter 41 and the second filter 42 may be moveably mounted within the housing 14 such that the first filter 41 and the second filter 42 may be selectively positioned in and out of the optical path 12 between the first aperture 27 and the second aperture 37. The first filter 41 and the second filter 42 each have optical attenuation spectra that may be calibrated and certified to a given measurement wavelength. In at least one embodiment, the first filter 41 and the second filter 42 may be National Institute of Standards and Technology (NIST) traceable calibration filters. In such embodiments, the filters 41, 42 are standards whose calibration is part of an unbroken chain of comparison with standards maintained by the NIST. The filters 41, 42 may be either neutral-density filters or color filters, depending upon the application for which the calibration unit 10 is to be used. Moreover, filters 41, 42 may be selected to attenuate any desired wavelength of light, including light in the ultraviolet, visible or infrared spectrums.

As shown in FIG. 1, in at least one embodiment, the first filter 41 may be mounted in a first pivot arm 46, which is affixed to a first shaft 48 enabling the first pivot arm 46 with the first filter 41 to rotated about the first shaft 48. Similarly, the second filter 42 may be mounted in a second pivot arm 47, which is affixed to a second shaft 49 enabling the second pivot arm 47 with the second filter 42 to rotated about the second shaft 49. The first shaft 48 and the second shaft 49 may be rotatably mounted in the first wall 28 of the housing 14 and extend through the first wall 28 such that each shaft 48, 49 is accessible externally of the housing 14.

A friction assembly 43 may be mounted on each shaft 48, 49 for holding the first and second filters 41, 42 in desired positions in which they are set by a technician. The friction assembly 43 may include bearing surfaces, o-rings and other features to facilitate holding each shaft 48, 49, and thereby the first and second filters 41, 42, in the desired positions. An outer end of each of the first shaft 48 and the second shaft 49 may include a slot 51 to facilitate manual rotation of the first shaft 48 and/or the second shaft 49 using a conventional screwdriver. The calibration unit 10 may further include set screws 44, which extend into the housing 14 and engage the first shaft 48 and the second shaft 49 separately to lock the first and second filters 41, 42 in their desired set positions.

The rotatable first shaft 48 and the second shaft 49 enable the first filter 41 and second filter 42, respectively, to be rotated independently and selectively from an operating position, which is out of the optical path 12, to a calibration position that is in the optical path 12. In the calibration position, the first filter 41 and/or the second filter 42 is positioned in the optical path 12 between the first aperture 27 and the second aperture 37. The first filter 41 and the second filter 42 may be arranged at a non-orthogonal angle to the optical path 12 to prevent significant back-reflection, which can generate optical noise and/or bias. In certain embodiments, the first filter 41 and the second filter 42 may be arranged at an angle of a few degrees from orthogonal relative to the optical path 12.

In their respective calibration positions, the first filter 41 and the second filter 42 are positioned in close proximity to the adjacent aperture, either the first aperture 27 or the second aperture 37, such that light emitted through the apertures 27, 37 entirely passes through the first filter 41 and/or the second filter 42 and is not incident on the first pivot arm 46 and/or second pivot arm 47, respectively, or on any other surface before passing through the first filter 41 and/or the second filter 42. Moreover, the first filter 41 and/or the second filter 42 have respective areas sufficiently extensive such that, in their calibration positions, light emitted through the apertures 27, 37 entirely passes through the filters 41, 42. For example, a diameter of the first filter 41 is large enough relative to its position adjacent either the aperture 27, 37 such that light emitted therethrough entirely passes through the first filter 41.

Figure 2A:
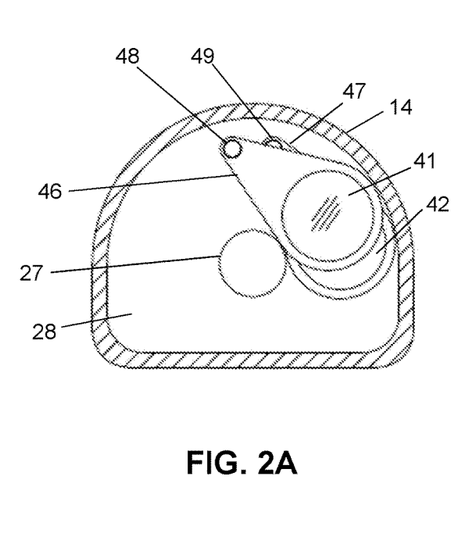
FIGS. 2A-2D show operational cross-sectional views taken along line A-A of FIG. 1.
Figure 2B:
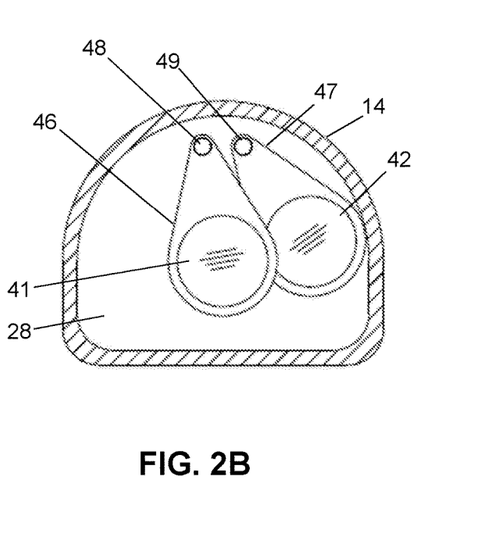
Figure 2C:
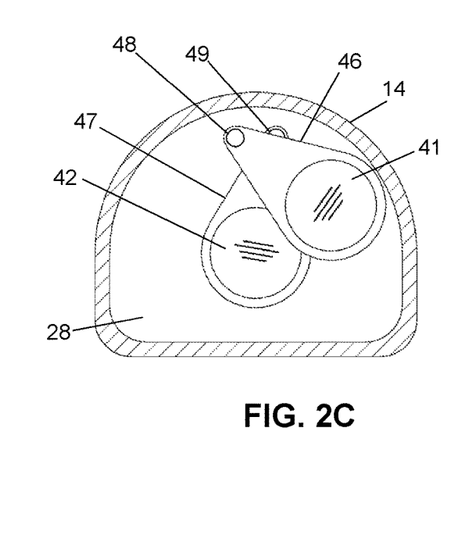
Figure 2D:
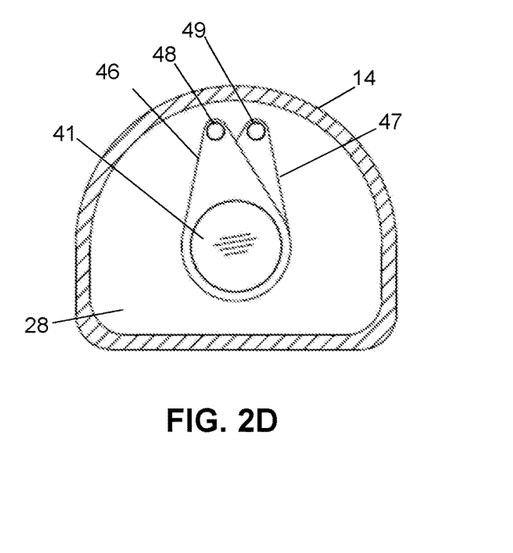

FIGS. 2A-2D show the first filter 41 and the second filter 42 in their operating and calibration positions. FIG. 2A shows both filters 41, 42 in the operating position, in which the filters 41, 42 are positioned out of the optical path 12 (i.e., out of the field of view of the first aperture 27 and the second aperture 37) and are protected from optical radiation by the housing 14. FIG. 2D shows both the first filter 41 and the second filter 42 in the calibration position, in which the filters 41, 42 are aligned with the optical path 12 and thereby the first aperture 27 and the second aperture 37. In FIG. 2B, only the first filter 41 is shown in the calibration position aligned with the first aperture 27 by rotation of the first pivot arm 46 by the first shaft 48, while the second filter 42 remains in the operating position. In FIG. 2C, only the second filter 42 is shown in the calibration position aligned with the first aperture 27 by rotation of the second pivot arm 47 by the second shaft 49, while the first filter 41 remains in the operating position.

Figure 3:
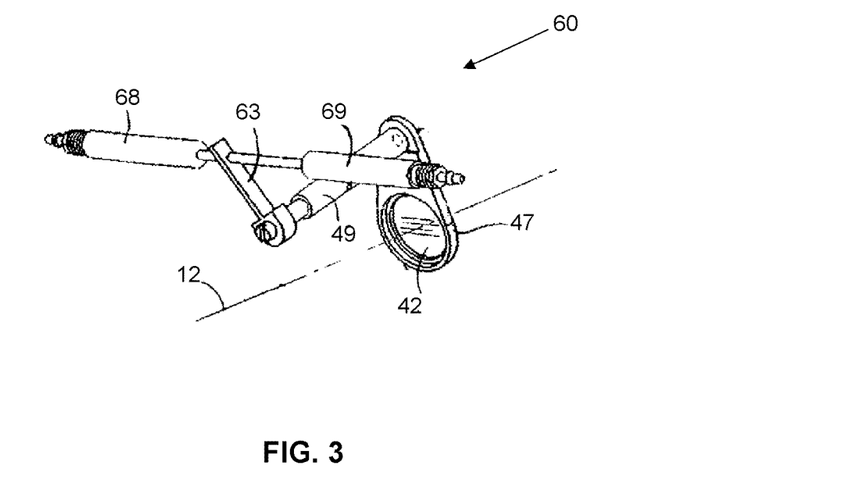
FIG. 3 shows a perspective view of filter mechanism according to an embodiment of the present disclosure.

In alternative embodiments, instead of being moved manually as shown in FIG. 1, the filters 41, 42 can be moved by pneumatic or electric actuators, such as solenoids, servo motors or stepper motors, connected to the first shaft 48 and the second shaft 49. FIG. 3 shows an exemplary embodiment of an exemplary actuator 60 for automated movement of the second filter 42. The actuator 60 may be disposed within the housing 14 (not shown in FIG. 3) or be attached thereto.

As shown in FIG. 3, an actuator arm 63 may be attached to the second shaft 49. The exemplary actuator 60 is a pneumatic actuator having pneumatic cylinders 68, 69 connected axially opposite one another to the actuator arm 63 and arranged to drive the actuator arm 63 back and forth, thereby rotating the second shaft 49 and the second filter 42. The pneumatic cylinders 68, 69 may be mounted in or to the housing 14. A second actuator (not shown) may be attached similarly to the first shaft 48 to enable movement of the first filter 41. In an alternative embodiment, the second actuator may be a different type of actuator than the exemplary actuator 60, and/or the first shaft 48 and the second shaft 49 may be actuated by different types of actuators, including at least one manual actuator. In certain embodiments, the actuator 60 may include an electric actuator, such as a solenoid, servo motor or stepper motor.

Figure 4:
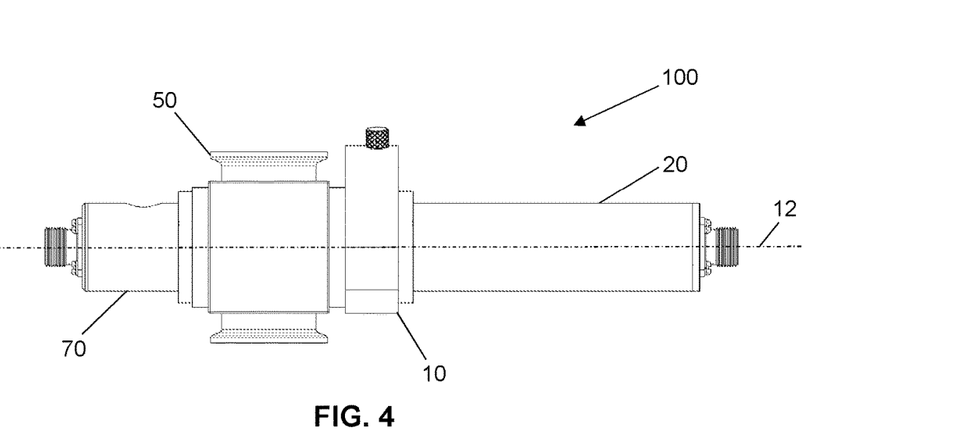
FIG. 4 shows an in-line sensor according to the present disclosure.
Figure 5:
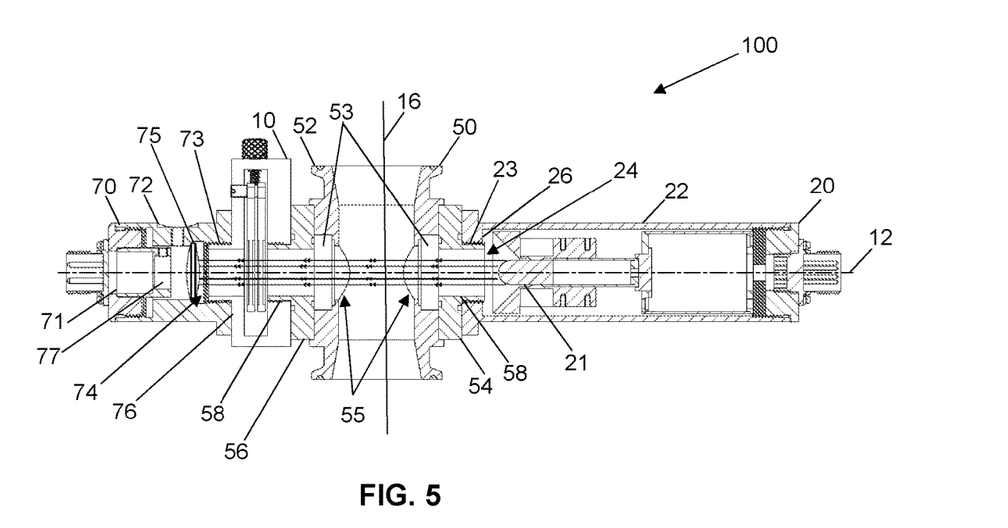
FIG. 5 shows a vertical, axial cross-sectional view of an alternative embodiment of an in-line sensor according to the present disclosure.

The calibration unit 10 may be employed in an in-line optical sensor 100, as shown in FIG. 4, to enable calibration of the in-line optical sensor 100 without removing the optical sensor 100 from the process. The optical sensor 100 may include the calibration unit 10, a lamp 20, a flow cell 50 and a detector unit 70, arranged such that the optical path 12 extends through each. As shown in FIG. 4, in one embodiment of the optical sensor 100, the detector 70 may be attached to one side of the flow cell 50, and the calibration unit 10 may be attached to the opposite side of the flow cell 50. In such an embodiment, the lamp 20 may be attached to the calibration unit 10 opposite the flow cell 50. In alternative embodiments of the optical sensor 100, as shown in FIG. 5, the calibration unit 10 may be attached between the flow cell 50 and the detector 70 on the side of the flow cell 50 opposite the lamp 20. In either configuration, the calibration unit 10 enables calibration of the optical sensor 100.

FIG. 5 shows a cross-sectional view of an embodiment the optical sensor 100 according to the present disclosure. As shown in FIG. 5, the flow cell 50 includes a body 52 having a flow path 16 extending therethrough. In certain embodiments, the flow path 16 defined by the body 52 may be generally cylindrical in form; however, other form factors are suitable for the body 52. The body 52 further includes a first flow cell fitting 54 and a second flow cell fitting 56 arranged generally orthogonal to the flow path 16 and aligned with the optical path 12. The first flow cell fitting 54 and the second flow cell fitting 56 each include a flow cell aperture 55 disposed in the optical path 12. The flow cell 50 may further include windows 53 disposed in each flow cell aperture 55, separating the flow cell apertures 55 from the flow path 16 extending through the body 52.

The first flow cell fitting 54 and the second flow cell fitting 56 each may include a flow cell connection 58 adjacent each flow cell aperture 55. The flow cell connections 58 are configured to enable various components to reversibly attach to the flow cell 50, including the calibration unit 10, the lamp 20 and the detector 70. The flow cell connections 58 are complementary to the unit connections 36, the lamp connection 23 and/or the detector connection 73. In at least one embodiment, the flow cell connections 58 are threaded connections complementary to threaded connections of the unit connections 36, a lamp connection 23 and/or a detector connection 73. In alternative embodiments, the flow cell connections 58 may be another suitable, reversible attachment means complementary to the flow cell connection 58, the lamp connection 23 and/or the detector connection 73.

The flow cell 50 is structured to enable a process medium to flow therethrough along the flow path 16 and to at least partially provide an optical path through the process medium flow. In at least one embodiment, the flow cell 50 is structured to at least partially provide the optical path 12 that is generally orthogonal to the flow path 16. The flow cell 50 enables process measurements to be performed on the process medium flowing through the flow cell 50, for example, determining a parameter of the process medium, such as the concentration of constituent of medium via an optical measurement. In such applications, the flow cell 50 may be inserted into a process line, and the lamp 20, detector 70 and/or calibration unit 10 attached to the flow cell 50 to provide the in-line optical sensor 100.

The lamp 20 includes a lamp housing 22 having a lamp end wall 26 including a lamp aperture 24 aligned with the optical path 12. The lamp end wall 26 may include the lamp connection 23 adjacent the lamp aperture 24 and configured to enable the lamp 20 to reversibly attach to various components, including the flow cell 50 and the calibration unit 10. The lamp connection 23 is complementary to the unit connections 36 and/or the flow cell connections 58. In at least one embodiment, the lamp connection 23 is a threaded connection complementary to threaded connections of the unit connections 36 and/or the flow cell connections 58. In alternative embodiments, the lamp connection 23 may be another suitable, reversible attachment means adjacent the lamp aperture 24 and complementary to the unit connections 36 and/or the flow cell connections 58.

The lamp 20 further includes a light source 21 within the lamp housing 22 such that light generated by the light source 21 is directed through the lamp aperture 24. The light source 21 may be an ultraviolet bulb, a light-emitting diode, a laser diode or any other suitable light source detectable by the detector 70.

The detector 70 includes a detector housing 72 having a detector end wall 76 including a detector aperture 74 aligned with the optical path 12. The detector end wall 76 may include the detector connection 73 adjacent the detector aperture 74 and configured to enable the detector 70 to reversibly attach to various components, including the flow cell 50 and the calibration unit 10. The detector connection 73 is complementary to the unit connections 36 and/or the flow cell connections 58. In at least one embodiment, the detector connection 73 is a threaded connection complementary to threaded connections of the unit connections 36 and/or the flow cell connections 58. In alternative embodiments, the detector connection 73 may be another suitable, reversible attachment means adjacent the detector aperture 74 and complementary to the unit connections 36 and/or the flow cell connections 58.

The detector 70 further includes a detector cell 71 within the detector housing 72 arranged such that light directed through the detector aperture 74 is incident upon and detected by the detector cell 71. The detector cell 71 may be a charge-coupled device, a photodiode or other suitable light sensitive device that is silicone or silicon carbide based. In certain embodiments, the detector 70 may include an objective lens 75 disposed within the detector housing 72 and configured to focus light directed through the detector aperture 74 upon the detector cell 71. In further embodiments, the detector 70 may include an optical filter 77 disposed between the lens 75 and the detector cell 71.

The calibration unit 10, as shown in FIG. 1, enables calibration of the in-line optical sensor 100, as shown in FIG. 4. For purposes of illustrating the calibration procedure, an exemplary first filter 41 may have an optical density of 0.5 OD and an exemplary second filter 42 may have an optical density of 1.0 OD. With a non-absorbing medium in the flow cell 50 and both the first filter 41 and the second filter 42 in their operating positions (e.g., as shown in FIG. 2A), an absorbance monitor connected to the detector 70 may be adjusted to yield a reading of 0.00. With the first filter 41 rotated to its calibration position and the second filter 42 in its operating position (e.g., as illustrated in FIG. 2B), the monitor reading should be 0.5 OD. When the first filter 41 is rotated to its operating position and the second filter 42 is rotated to its calibration position (e.g., as shown in FIG. 2C), the monitor reading should be 1.0 OD. Finally, when both the first filter 41 and the second filter 42 are rotated to their calibration positions (e.g., as shown in FIG. 2D), the monitor will read the sum of the two filter densities, namely 1.5 OD. This three-point calibration procedure determines both accuracy and linearity of the optical system.

The calibration unit 10 enables calibration of an in-line optical sensor 100 without removing the optical sensor 100 from the process. Relative to conventional detectors having calibration systems built into a detector housing or requiring separately installed filters, the calibration unit 10 may be employed in a wider variety of processes. Because the calibration unit 10 may be reversibly attached to either side of the flow cell 50, the calibration unit 10 may be used to calibrate multiple sensors situated at most any measuring point in a process. For example, relative to conventional detectors, the compact form factor of the calibration unit 10 enables the calibration unit 10 to be used at measuring points with tight space constraints. Moreover, the calibration unit 10 may be attached to either side of the flow cell 50 depending on which side of the measuring point has sufficient space for both the calibration unit 10 and a process technician to access the sensor to be calibrated, regardless of which side includes the detector. Further, the calibration unit 10 may be moved from sensor to sensor by the technician to calibrate multiple sensors using a single calibration unit 10.

The calibration unit 10 may be used to calibrate a wide variety of sensors, particularly older sensors that do not have built-in calibration systems, which enables more convenient calibration and better flexibility for reliably monitoring the process without the cost of replacing older sensors. The calibration unit 10 may be used to facilitate calibration of any type of absorption-measuring optical sensor having a light source and detector.

Figure 6:
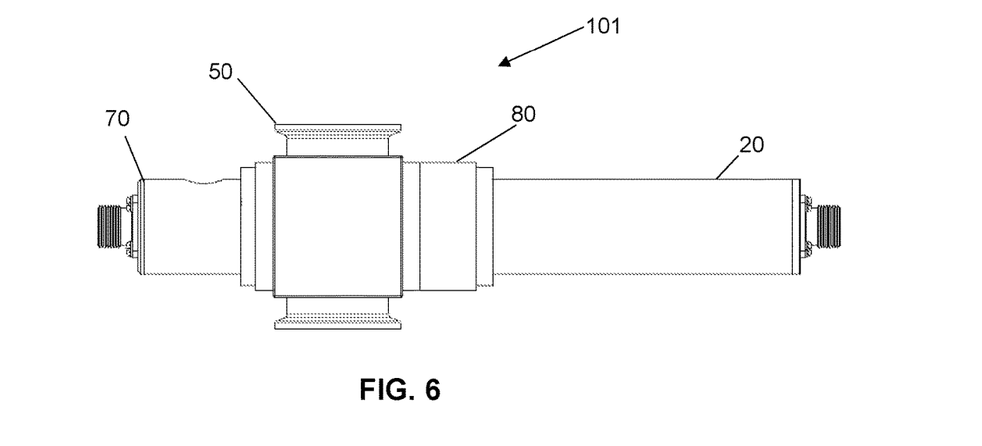
FIG. 6 shows an in-line sensor having a spacer according to the present disclosure.

A path length of the optical path 12 through the calibration unit 10 may be about 5 mm, which may not be significantly greater than a path length from the light source 21 of the lamp 20 to the detector cell 71 of the detector 70 in absence of the calibration unit 10. In certain applications of the calibration unit 10, the increased path length of applying the calibration unit 10 may not affect the calibration of the optical sensor 100. However, in certain applications of the calibration unit 10, the accuracy of the calibration may be sensitive to changes in the path length of the optical path 12 between the light source 21 and the detector cell 71. Consequently, in such applications, if the calibration unit 10 were removed from the optical sensor 100 after the calibration procedure (e.g., to be used to calibrate a different sensor), the readings generated by the optical sensor 100 may not be accurate. In such instances, an in-line optical sensor 101 may include a spacer 80 disposed in the optical sensor 101 at the same position where the calibration 10 was positioned during the calibration procedure. FIG. 6 shows the optical sensor 101 having the flow cell 50, lamp 20, the detector 70 and the spacer 80, in place of the calibration unit 10, disposed between the flow cell 50 and the lamp 20.

Similar to the calibration unit 10, the spacer 80 may be attached to either side of the flow cell 50. For example, as shown in FIG. 7, the spacer 80 may be attached to the flow cell 50 adjacent the detector 70 in instances where the calibration unit 10 had been attached to the flow cell 50 adjacent the detector 70 during the calibration procedure.

Figure 7:
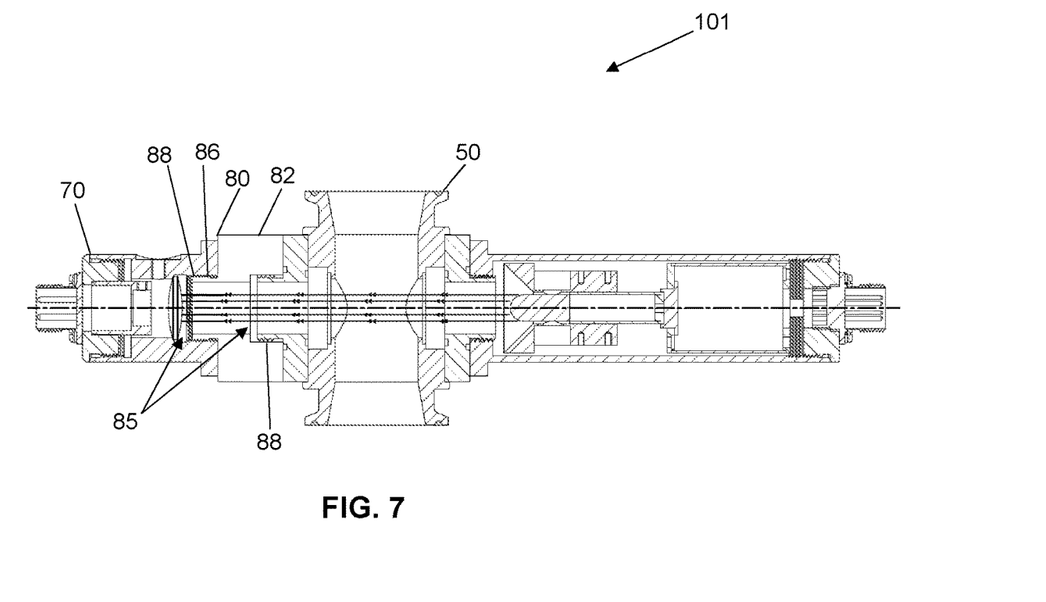
FIG. 7 shows a vertical, axial cross-sectional view of an in-line sensor having a spacer according to the present disclosure.

As shown in FIG. 7, the spacer 80 may include a spacer body 82 having apertures 85 aligned along the optical path 12. The body 82 may include a spacer fitting 86 defining one of the apertures 85 and extending in the general direction of the optical path 12. The spacer body 82 includes spacer connections 88 adjacent the apertures 85 configured to enable the spacer 80 to reversibly attach to various components, including the flow cell 50, lamp 20 and the detector 70. The connections 88 are complementary to the flow cell connection 58, the lamp connection 23 and/or the detector connection 73. In at least one embodiment, the connection 88 is a threaded connection complementary to threaded connections of the flow cell connection 58, the lamp connection 23 and/or the detector connection 73. In alternative embodiments, the connection 88 may be another suitable, reversible attachment means complementary to the flow cell connection 58, the lamp connection 23 and/or the detector connection 73.

The spacer 80 is sized to directly replace the calibration unit 10. Accordingly, the body 82 and spacer connections 88 are complementary to the housing 14 and the unit connections 36, respectively. In at least one embodiment, the spacer 80 has the same optical path length as the calibration unit 10.

While various embodiments of a calibration unit, an in-line optical sensor and methods for using and constructing the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible and still remain within the scope of the present disclosure.

We claim:

1. A device for calibrating an in-line sensor, comprising:
a housing having a first aperture and a second aperture therethrough, the first aperture and the second aperture defined by corresponding housing walls and arranged along an optical path extending through the housing;
a first filter disposed within the housing such that the first filter is moveable from an operating position to a calibration position, wherein in the calibration position the first filter is arranged in the optical path; and
a second filter disposed within the housing such that the second filter is moveable, independently from and adjacent to the first filter, from an operating position to a calibration position, wherein in the calibration position the second filter is arranged in the optical path,
wherein the housing includes a connection adjoining and at least partially defining each of the first aperture and the second aperture, each connection integral with the housing wall defining its corresponding aperture and structured to enable the housing to be reversibly attached to a flow cell, a detector and a light source of an in-line sensor.

2. The device of claim 1, wherein the first filter is attached to a rotatable first shaft such that the first filter is rotatable from the operating position to the calibration position via rotation of the first shaft.

3. The device of claim 2, wherein the first filter is connected to a first arm that is connected to the first shaft such that rotation of the first shaft enables rotation of the first filter, and wherein the first shaft extends through the first wall of the housing.

4. The device of claim 1, wherein the second filter is attached to a rotatable second shaft such that the second filter is rotatable from the operating position to the calibration position via rotation of the second shaft.

5. The device of claim 4, wherein the second filter is connected to a second arm that is connected to the second shaft such that rotation of the second shaft enables rotation of the second filter, and wherein the second shaft extends through the first wall of the housing.

6. The device of claim 1, wherein the first filter and the second filter are neutral-density filters.

7. The device of claim 1, wherein the first filter and the second filter are calibration elements traceable to standards maintained by the National Institute of Standards and Technology.

8. The device of claim 1, wherein each connection is a threaded connection complementary to threaded connections of the flow cell, the detector and the light source.

9. The device of claim 1, wherein the housing includes a fitting, which defines the first aperture, extending from a first wall of the housing, and wherein the fitting includes the connection adjacent the first aperture.

10. The device of claim 1, wherein a second wall of the housing includes the second aperture, and wherein the second wall includes the connection adjacent the second aperture on an edge of the second wall.

11. The device of claim 1, further comprising:
a first actuator connected to the first filter via a first arm connected to a rotatable first shaft such that the first filter is rotatable from the operating position to the calibration position via rotation of the first shaft; and
a second actuator connected to the second filter via a second arm connected to a rotatable second shaft such that the second filter is rotatable from the operating position to the calibration position via rotation of the second shaft,
wherein the first actuator and second actuator are each remotely operable.

12. An in-line sensor for determining a parameter of a process medium flow, the sensor comprising:
a light source embodied to generate light along an optical path, the light source including a source aperture disposed along the optical path and a connection adjacent the source aperture;
a detector arranged in the optical path and embodied to detect the light generated by the light source, the detector including a detector aperture disposed along the optical path and a connection adjacent the detector aperture;
a flow cell disposed between and reversibly attachable via complementary connections to the light source and the detector, the flow cell having opposing sides including opposing apertures therethrough and in the optical path adjacent the complementary connections, the flow cell further embodied to enable a fluid to be analyzed to flow along a flow path, the flow path generally orthogonal to the optical path; and a calibration unit reversibly attachable to either side of the flow cell via the complementary connections and disposed between the light source and the detector and in the optical path, wherein the calibration unit includes:

a housing having a first aperture and a second aperture therethrough, the first aperture and the second aperture defined by corresponding housing walls and arranged along an optical path extending through the housing by an optical path length;

a first filter disposed within the housing such that the first filter is moveable from an operating position to a calibration position, wherein in the calibration position the first filter is arranged in the optical path; and a second filter disposed within the housing such that the second filter is moveable, independently from and adjacent to the first filter, from an operating position to a calibration position, wherein in the calibration position the second filter is arranged in the optical path, wherein the housing includes a connection adjoining and at least partially defining each of the first aperture and the second aperture, each connection integral with the housing wall defining its corresponding aperture and structured to enable the housing to be reversibly attached to a flow cell, a detector and a light source.

13. The in-line sensor of claim 12, further comprising a spacer in substitution of the calibration unit, the spacer including a spacer housing having a first spacer aperture and a second spacer aperture therethrough, the first spacer aperture and the second spacer aperture arranged along an optical path extending through the housing, wherein the spacer housing includes a connection adjacent each of the first spacer aperture and the second spacer aperture, the connection structured to enable the spacer to be reversibly attached to the flow cell, the detector and the light source, and wherein the spacer has the same optical path length as the calibration unit.

14. The in-line sensor of claim 12, wherein the first filter is attached to a rotatable first shaft such that the first filter is rotatable from the operating position to the calibration position via rotation of the first shaft.

15. The in-line sensor of claim 14, wherein the first filter is connected to a first arm that is connected to the first shaft such that rotation of the first shaft enables rotation of the first filter, and wherein the first shaft extends through the first wall of the housing.

16. The in-line sensor of claim 12, wherein the second filter is attached to a rotatable second shaft such that the second filter is rotatable from the operating position to the calibration position via rotation of the second shaft.

17. The in-line sensor of claim 16, wherein the second filter is connected to a second arm that is connected to the second shaft such that rotation of the second shaft enables rotation of the second filter, and wherein the second shaft extends through the first wall of the housing.

18. The in-line sensor of claim 12, wherein the first filter and the second filter are neutral-density filters.

19. The in-line sensor of claim 12, wherein the first filter and the second filter are calibration elements traceable to standards maintained by the National Institute of Standards and Technology.

20. The in-line sensor of claim 12, wherein each connection is a threaded connection complementary to threaded connections of the flow cell, the detector and the light source.

* * * * *